United States Patent [19]
Moretti

[11] Patent Number: 6,037,372
[45] Date of Patent: Mar. 14, 2000

[54] USE OF AN ALKANOYL-L-CARNITINE FOR THE TREATMENT OF GLUTAMATE MEDIATED DISEASES

[75] Inventor: Sonia Moretti, Rome, Italy

[73] Assignees: Sigma-Tau Industrie Farmaceutiche Riunite S.p.A.; Mendes s.r.l., both of Rome, Italy

[21] Appl. No.: 09/147,034

[22] PCT Filed: Mar. 12, 1997

[86] PCT No.: PCT/IT97/00056

§ 371 Date: Sep. 15, 1998

§ 102(e) Date: Sep. 15, 1998

[87] PCT Pub. No.: WO97/34596

PCT Pub. Date: Sep. 25, 1997

[30] Foreign Application Priority Data

Mar. 15, 1996 [IT] Italy .................................. RM96A0171

[51] Int. Cl.[7] .................................................. A61K 31/225

[52] U.S. Cl. .............................................................. 514/547
[58] Field of Search ............................................... 514/547

[56] References Cited

U.S. PATENT DOCUMENTS 4,194,006  3/1980  Cavazza .

FOREIGN PATENT DOCUMENTS 0 376 899  7/1990  European Pat. Off. .
0 498 144  8/1992  European Pat. Off. .
WO 95/00137  1/1995  WIPO .

*Primary Examiner*—Raymond Henley, III
*Attorney, Agent, or Firm*—Oblon, Spivak, McClelland, Maier & Neustadt, P.C.

[57] ABSTRACT

The use of an alkanoyl-L-carnitine, e.g., acetyl-L-carnitine, or a pharmacologically acceptable salt thereof is disclosed to produce a medicament for the therapeutic treatment or prophylaxis of glutamate-mediated cytological disturbances or diseases.

7 Claims, No Drawings

USE OF AN ALKANOYL-L-CARNITINE FOR THE TREATMENT OF GLUTAMATE MEDIATED DISEASES

This application is a 371 of PCT/IT97/00056 filed Mar. 12, 1997.

The present invention relates to a novel therapeutic use of an alkanoyl L-carnitine (as defined hereinbelow) or a pharmacologically acceptable salt thereof for the therapeutic treatment or prophylaxis of glutamate-mediated disturbances or diseases. More particularly, the present invention relates to the therapeutic treatment with an alkanoyl L-carnitine or a pharmacologically acceptable salt thereof of individuals in whom glutamate contributes towards the pathogenesis of a particular disease or gives rise to cytological disturbances, or alternatively to the prophylaxis of such diseases or disturbances.

Glutamate is a non-essential and glucogenic amino acid which is in equilibrium with α-ketoglutarate. It forms the amide, glutamine, by incorporating ammonia. By transamination, glutamine can give its amine group to various keto acids to form α-ketoglutaramate. The latter is then hydrolysed to α-ketoglutarate and ammonia by the action of a specific diaminase. The concentration of L-glutamate in peripheral blood ranges between 141 and 311 μmol/L. Increased extracellular concentrations of glutamate can competitively inhibit the membrane transport of cystine into the cell, with consequent oxidative damage. High levels of glutamate are present in many morbid conditions, as already demonstrated by White in 1952 (White J. M. et al., *J. Clin. Lab. Med.* 40:703, 1952). It is, however, emphasized that high levels of glutamate were observed in individuals with tumours in the digestive apparatus, bronchial carcinomas, malignant lymphomas, Hodgkin's disease and breast and ovary tumours (Beaton J. R. et al., *Can. Med. Ass. J.* 65:219, 1951). Recently, high levels of glutamate have also been found in the plasma of individuals with HIV (human immunodeficiency virus) infections (Droge W. et al., *J. Cancer. Res. Clin. Oncol.* 114:124, 1988). In the central nervous system, it has been demonstrated that high concentrations of glutamate contribute towards neuronal damage by excitotoxic mechanisms, following binding of glutamate to the NMDA (N-methyl-D-aspartate) receptors, and on account of oxidative stress, following competition for the uptake of cystine by neurons (Dewhurst S. et al., *Molecular Medicine Today* 1:16, 1996).

From that which has been outlined above, it is evident that variations in the concentration or in the metabolism of glutamate can contribute towards the pathogenesis of many diseases or give rise to cytological disturbances. Examples of diseases or disturbances characterized by altered levels of glutamate include cancer, infection with HIV, immunodeficiencies, drug dependencies, headaches, chronic fatigue syndrome, schizophrenic disorders, epilepsy, amyotrophic lateral sclerosis and other motor neuron diseases and peripheral neuropathies, senile and presenile dementias, apoplexy and sequences thereof, cerebrovascular ischaemic diseases, decreased cerebral flow and altered cerebral metabolism, neurodegenerative diseases, Huntington's disease, Parkinson's disease, prion protein diseases, meningoencephalitis, and Chinese restaurant syndrome.

The use of certain substances can also give rise to high levels of glutamate. Examples of such substances are cocaine and sulpiride.

According to the present invention, the administration of an alkanoyl L-carnitine wherein the alkanoyl group has 2–6 carbon atoms or a pharmacologically acceptable salt thereof can alleviate glutamate-mediated cytological disturbances.

Preferably, the alkanoyl L-carnitine is selected from the group comprising acetyl-, propionyl-, butyryl-, valeryl- and isovaleryl-L-carnitine.

In the description which follows, the expression pharmacologically acceptable salt of an alkanoyl L-carnitine is understood to refer to any salt of the latter with an acid which does not give rise to undesired toxic effects or side effects. These acids are well known to pharmacologists and to persons skilled in the pharmaceutical field.

Non-limiting examples of such salts are: chloride; bromide; iodide; aspartate, particularly hydrogen aspartate; citrate, particularly hydrogen citrate; tartrate; phosphate, particularly hydrogen phosphate; fumarate, particularly hydrogen fumarate; glycerophosphate, glucose phosphate; lactate; maleate, particularly hydrogen maleate; orotate; oxalate, particularly hydrogen oxalate; sulphate, particularly hydrogen sulphate; trichloroacetate, trifluoroacetate and methanesulphonate.

For the sake of simplicity and clarity, hereinbelow reference will be made to acetyl L-carnitine only, it being understood, however, that whatever disclosed and claimed in connection with acetyl L-carnitine equally applies to all of the above-identified alkanoyl L-carnitines and the pharmacologically acceptable salts thereof, which may be used alone or as a mixture thereof.

According to the present invention, 50 mg–15 g per day, preferably 500 mg–10 g per day, of alkanoyl L-carnitines or an equivalent amount of pharmacologically acceptable salts thereof are administered orally or parenterally for the treatment or prophylaxis of glutamate-mediated diseases or disturbances.

Also according to the present invention, alkanoyl L-carnitines or pharmacologically acceptable salts thereof can be administered in combination with cortisone medicaments, antioxidants, anti-inflammatory agents, immunomodulatory agents, cytostatic agents, immunological agents, endocrinological agents, vascular agents or vasodilators.

Still according to the present invention, a pharmaceutical composition is provided which can be administered orally or parenterally for the therapeutic treatment or prophylaxis of glutamate-mediated cytological disturbances or diseases, this composition comprising as active principle an amount of an alkanoyl L-carnitine, or pharmacologically acceptable salts thereof, which is effective for reducing the levels of glutamate, and at least one pharmacologically acceptable excipient. The composition may also advantageously comprise the medicaments listed above.

Previous therapeutic uses of acetyl L-carnitine for the therapeutic treatment of myocardial arrhythmia and ischaemia, of functional peripheral vasculopathies of the arteries, of senile dementia and of peripheral neuropathies are already known.

For all the known therapeutic uses, the daily dose administered is from about 2 to about 20 mg of L-carnitine or an equivalent amount of a pharmacologically acceptable salt thereof/kg of body weight/day.

However, there is no correlation between the known therapeutic uses of acetyl L-carnitine mentioned above and that which constitutes the subject of the present invention.

It has now been found, surprisingly, that acetyl L-carnitine and analogues (despite the technical prejudice arising from the prior publications and patents) are capable of reducing the levels of glutamate in human biological fluids. It is emphasized by ample supporting scientific literature that the mechanism of action of acetyl L-carnitine was focused at the cerebral level, whereas, in the present invention, a loading action of the metabolism of glutamate is also demonstrated at the systemic level.

The examples which follow are intended to illustrate the invention and should not in any way be understood as limiting the scope thereof.

EXAMPLE 1

Twelve individuals infected with HIV were enroled. Blood was taken before and after oral treatment with acetyl L-carnitine at a dose of 3 g/day for 4 weeks. The glutamate was measured by a colorimetric method according to Beutler (Beutler O. H. et al., Methods of Enzymatic Analysis Vol. IV, page 1708, 1974), and the results were expressed as L-glutamate per $\mu$mol/L.

TABLE 1

| Patient | Before | After |
|---------|--------|-------|
| #1 | 202 | 161 |
| #2 | 169 | 153 |
| #3 | 534 | 161 |
| #4 | 518 | 250 |
| #5 | 356 | 178 |
| #6 | 348 | 161 |
| #7 | 340 | 120 |
| #8 | 138 | 50 |
| #9 | 299 | 186 |
| #10 | 194 | 153 |
| #11 | 485 | 234 |
| #12 | 299 | 81 |
| AVERAGE | 323.5000 | 157.3333 |
| Standard deviation | 135.2321 | 56.0298 |
| Student test | | 0.0001 |

It is known that HIV-infected individuals can have varying levels of glutamate in the plasma. The experiments reported here demonstrated that the oral administration of acetyl L-carnitine reduces the levels of glutamate in the peripheral blood, independently of the fact that the patient might have normal or increased levels of glutamate in his or her blood.

EXAMPLE 2

A female patient with a previous history of drug dependency, with chronic hepatopathy from hepatitis C virus, with HIV antibodies, who exhibited pronounced asthenia, lacking strength in the lower limbs with paraesthesia and difficulty in walking diagnosed as "axial cerebellar and tetrapyramidal syndrome" and who, under magnetic resonance examination, exhibited an "enlargement of the supra-tentorial ventricular system, with predominance of the left lateral ventricle and moderate enlargement of the subarachnoid spaces as in atrophy with predominant subcortical expression" underwent a parenteral treatment with acetyl L-carnitine at a dose of 3 g/day for 4 weeks. Before and after the treatment, the glutamate in the plasma and in the cerebrospinal fluid was assayed.

The results demonstrated a reduction in the glutamate in the blood from 201 $\mu$mol/L to 125 $\mu$mol/L and in the fluid from 62 $\mu$mol/L to 16 $\mu$mol/L.

This example confirms that treatment with acetyl L-carnitine can reduce the levels of glutamate in the cerebrospinal fluid and in the blood.

We claim:

1. A process for the therapeutic treatment or prophylaxis of glutamate-mediated cytological disturbances or diseases by reducing the levels of glutamate in cerebral spinal fluid and in blood, comprising administering to a subject an effective amount for such treatment or prophylaxis of an alkanoyl L-carnitine wherein the alkanoyl group has 2–6 carbon atoms or a pharmacologically acceptable salt thereof.

2. The process of claim 1, wherein the alkanoyl L-carnitine is selected from the group consisting of acetyl-, propionyl-, butyryl-, valeryl- and isovaleryl-L-carnitine.

3. The use of claim 1 or 2, wherein the glutamate-mediated cytological disturbances or diseases are cancer, immunodeficiencies, drug dependencies, headaches, chronic fatigue syndrome, schizophrenic disorders, epilepsy, amyotrophic lateral sclerosis and other motor neuron diseases and senile and presenile dementias, apoplexy and sequences thereof, cerebrovascular ischaemic diseases, decreased cerebral flow and neurodegenerative diseases, Huntington's disease, Parkinson's disease, prion protein diseases, meningoencephalitis, and Chinese restaurant syndrome.

4. The process of claim 1, or 2, wherein the alkanoyl L-carnitine or the pharmacologically acceptable salt thereof is administered in combination with cortisone medicaments, antioxidants, anti-inflammatory agents, immunomodulatory agents, cytostatic agents, immunological agents, endocrinological agents, vascular agents or vasodilators.

5. The process of claim 1 or 2, which comprises the oral or parenteral administration of 50 mg–15 g per day of the alkanoyl L-carnitine or an equivalent amount of the pharmacologically acceptable salt thereof.

6. The process of claim 5, which comprises the oral or parenteral administration of 500 mg–10 g per day of the alkanoyl L-carnitine or an equivalent amount of the pharmacologically acceptable salt thereof.

7. The process of claim 1 or 2, wherein the alkanoyl L-carnitine is acetyl L-carnitine.

* * * * *